United States Patent [19]

Nakamura et al.

[11] Patent Number: 5,629,443
[45] Date of Patent: May 13, 1997

[54] HIGHLY PURIFIED ACETONITRILE AND PROCESS FOR PURIFYING CRUDE ACETONITRILE

[75] Inventors: Shigeo Nakamura, Yokohama; Shigeru Kurihara, Kawasaki; Minoru Saitoh, Yokohama; Hideo Midorikawa, Kurashiki, all of Japan

[73] Assignee: Asahi Kasei Kogyo Kabushiki Kaisha, Osaka, Japan

[21] Appl. No.: 371,180

[22] Filed: Jan. 11, 1995

Related U.S. Application Data

[63] Continuation of PCT/JP93/00638, May 14, 1993.

[51] Int. Cl.$^6$ ................................................. C07C 253/34
[52] U.S. Cl. ................................................................ 558/435
[58] Field of Search ........................................................ 558/435

[56] References Cited

U.S. PATENT DOCUMENTS

| | | | |
|---|---|---|---|
| 3,322,814 | 5/1967 | Iappelli | 558/435 |
| 4,119,497 | 10/1978 | Ocampo et al. | 558/435 X |
| 4,287,134 | 9/1981 | Smiley | 558/435 |
| 4,308,108 | 12/1981 | Higuchi et al. | 558/435 |
| 4,328,075 | 5/1982 | Fitzgibbons et al. | 558/435 X |
| 5,250,721 | 10/1993 | Cesa et al. | 558/435 |
| 5,292,919 | 3/1994 | Himes et al. | 558/435 |
| 5,426,208 | 6/1995 | Himes et al. | 558/435 |

FOREIGN PATENT DOCUMENTS

| | | | |
|---|---|---|---|
| 217212 | 1/1995 | Germany | 558/435 |
| 51-32518 | 3/1976 | Japan | 558/435 |
| 5-140070 | 6/1993 | Japan | 558/435 |
| 1318588 | 6/1987 | U.S.S.R. | 558/435 |
| 1810332 | 4/1993 | U.S.S.R. | 558/435 |
| 2249308 | 5/1992 | United Kingdom | 558/435 |
| WO93/23366 | 11/1993 | WIPO . | |

*Primary Examiner*—Johann Richter
*Assistant Examiner*—John Peabody
*Attorney, Agent, or Firm*—Pennie & Edmonds

[57] ABSTRACT

A process for purifying crude acetonitrile comprising: (1) a step of contacting crude acetonitrile with nascent oxygen, (2) a step of contacting the acetonitrile from step (1) with a solid base, and (3) a step of removing low-boiling compounds and high-boiling compounds from the acetonitrile from step (2), wherein the step (3) may be effected after the step (1) and before the step (2).

29 Claims, 2 Drawing Sheets

HIGHLY PURIFIED ACETONITRILE AND PROCESS FOR PURIFYING CRUDE ACETONITRILE

This application is a continuation of PCT/JP93/00638 (filed May 14, 1993).

FILED OF THE INVENTION

This invention relates to a process for purifying crude acetonitrile. More particularly, it relates to a purification process for obtaining highly purified acetonitrile having a small absorbance in the ultraviolet region at a wavelength of from 200 to 400 nm, which is suitable for use as a solvent of a mobile phase of liquid chromatography, particularly high performance liquid chromatography (HPLC).

BACKGROUND OF THE INVENTION

Acetonitrile on the current market is mostly prepared by purifying crude acetonitrile recovered as a by-product in the production of acrylonitrile or methacrylonitrile comprising catalytic ammoxydation of propylene or isobutene with ammonia and molecular oxygen Since the by-produced acetonitrile contains many impurities, various processes of purification have conventionally been proposed as follows.

Known processes for removing allyl alcohol from crude acetonitrile include reaction with sulfuric acid followed by distillation (JP-A-51-23218, the term "JP-A as used herein means an "unexamined published Japanese patent application"), extractive distillation in the presence of water (JP-A-55-143949), and reaction with an aqueous solution of an alkali metal or alkaline earth metal hypochlorite (JP-A-51-32518). Known processes for removing oxazole from crude acetonitrile include reaction with molecular chlorine followed by separation (JP-A-59-10556) and extractive distillation in the presence of water (JP-A-55-143950).

Known processes for purifying crude acetonitrile include reaction with a basic compound followed by distillation (JP-A-56-5449) and distillation using three distillation columns (JP-A-58-124751) In short, the by-product acetonitrile contains allyl alcohol, oxazole, acrylonitrile, etc. as main impurities and, in order to remove these impurities it has been necessary to combine some of these processes proposed to date, making the whole purification process very complicated. Moreover, the present inventors verified by experiments that each of these known processes fails to afford acetonitrile having an absorbance of not more than 0.05 at 200 to 400 nm.

East German Patent DD217212A1 discloses an excellent purification process comprising contacting crude acetonitrile with ozone to simultaneously decompose allyl alcohol, oxazole, acrolein, etc. and separating purified acetonitrile by distillation However, as a result of verification experiments on this process, the present inventors revealed that the process really succeeds in reducing the absorbance at 200 to 400 nm to some extent but not to 0.05 or less.

Therefore, commercially available acetonitrile is unsatisfactory as a mobile phase solvent for liquid chromatography, particularly HPLC due to its high UV (200 to 400 nm) absorbance. It has thus been demanded to develop an industrially beneficial process for preparing acetonitrile having sufficient purity for use as a mobile phase solvent for liquid chromatography The UV absorption of crude acetonitrile at 200 to 400 nm is chiefly ascribed to the double bonds of impurities due to the production process. For example, compounds having a carbon-to-carbon double bond, a carbonyl group (C=O), a carboxyl group (COOH), an aldehyde group (CHO), a carbon-to-nitrogen double bond, a nitroso group (N=O), a nitro group ($NO_2$) or a like bond or functional group, exhibit absorption in that wavelength region. Examples of compounds with such a bond or a functional group are allyl alcohol, oxazole, acrylonitrile, methacrylonitrile, cis- and trans-crotononitrile, acrylic acid, methyl acrylate, methacrylic acid, methyl methacrylate, acetic acid, acrolein, methacrolein, and acetone. It is very difficult to remove these compounds to reduce the absorbance at 200 to 400 nm to 0.05 or less. More specifically, in order to reduce the absorbance of acetonitrile at 200 nm to 0.05 or less, the acetonitrile must have its allyl alcohol content reduced to 1.5 ppm or less; its oxazole content to 0.8 ppm or less; its acrylonitrile content to 0.2 ppm or less; its methacrylonitrile content to 0.2 ppm or less; its cis-crotononitrile content to 0.2 ppm or less; its acrylic acid content to 0.2 ppm or less; its methyl acrylate content to 0.2 ppm or less; and its acetic acid content to 30 ppm or less. The same strict requirement applies to other impurities. Because crude acetonitrile usually contains no less than two of these compounds, the critical content of each compound would actually be lower than the above value. Accordingly, obtaining highly purified acetonitrile admittedly requires high techniques.

SUMMARY OF THE INVENTION

An object of the present invention is to provide a process for purifying crude acetonitrile for producing highly purified acetonitrile which has a UV absorbance of not more than 0.05 at 200 to 400 nm and is useful as a solvent of a mobile phase of liquid chromatography, particularly HPLC.

Other objects and effects of the present invention will be apparent from the following description.

As a result of extensive investigations on a contact treatment of acetonitrile with ozone, the present inventors have found that a contact treatment with ozone produces acids and permanganate reducing substances and that these substances can be removed by contact with a solid base, and based on these findings, completed a simple and easy process for purifying acetonitrile. They have also found a surprising fact that highly purified acetonitrile having an absorbance of not more than 0.05 at a wavelength of from 200 to 400 nm can be obtained by bringing a liquid after a contact treatment with ozone into contact with a solid base and then removing compounds having lower and higher boiling points than acetonitrile (hereinafter simply referred to as low-boiling compounds and high-boiling compounds, respectively). The inventors have thus reached the present invention based on these findings.

The present invention provides a process for purifying crude acetonitrile comprising:

(1) a step of contacting crude acetonitrile with nascent oxygen, (2) a step of contacting the acetonitrile from step (1) with a solid base, and (3) a step of removing low-boiling compounds and high-boiling compounds from the acetonitrile from step (2), wherein the step (3) may be effected after the step (1) and before the step (2).

DETAILED DESCRIPTION OF THE INVENTION

The crude acetonitrile which can be purified by the process of the present invention includes crude acetonitrile having a absorbance of not less than 0.1 at a wavelength of 200 nm. The crude acetonitrile may be acetonitrile by-produced in the production of acrylonitrile or methacrylonitrile comprising catalytic ammoxydation of propylene, isobutene or t-butyl alcohol with ammonia and molecular oxygen.

Of the crude acetonitrile species having a UV absorbance of not less than 0.1 at 200 nm, preferred is crude acetonitrile having a UV absorbance of from 0.1 to 5, and more preferably of from 0.1 to 3, at 200 nm.

The crude acetonitrile is not particularly limited, and those produced by other methods can be used. For example, crude acetonitrile obtained by an ammoxydation reaction of a saturated hydrocarbon compound, such as ethane, propane, butane, isobutane or pentane, carbon monoxide, an aromatic compound, such as toluene or xylene, etc. can also be used.

According to the process of the present invention, acetonitrile having a UV absorbance of not more than 0.05 at 200 to 400 nm can be obtained from crude acetonitrile having a UV absorbance of not less than 0.1 at 200 nm.

While the process may be applied to crude acetonitrile having a UV absorbance of less than 0.1 at 200 nm, such produces a small effect and is not so attractive chiefly from the economical viewpoint.

The terminology "UV absorbance (or simply absorbance)" as used in the present invention means a value measured in a quartz cell having an optical path of 10 mm using distilled water for liquid chromatography as a reference at a prescribed wavelength of detection.

Step (1) of the process of the present invention consists of contacting crude acetonitrile with nascent oxygen. The purpose of step (1) resides in decomposition of impurities having a double bond which are difficult to remove by distillation, adsorption or reaction, particularly allyl alcohol, oxazole, and acrylonitrile, by contact with nascent oxygen to convert them into compounds which are ready to be separated and removed in the subsequent step. Compounds capable of generating nascent oxygen include permanganic acid or salts thereof (e.g., potassium permanganate), peroxides (e.g., hydrogen peroxide, sodium peroxide, and barium peroxide), oxy acids or salts thereof (e.g., sodium hypochlorite, potassium hypochlorite, sodium hypoiodite, potassium hypoiodite, sodium hypobromite, potassium hypobromite, sodium chlorate, potassium chlorate, sodium iodate, potassium iodate, sodium bromate, potassium bromate, sodium perchlorate, potassium perchlorate, perchloric acid, periodic acid, sodium periodate, and potassium periodate), and an ozone-containing gas, with an ozone-containing gas being preferred. By step (1), the efficiency of separation and removal of impurities in the subsequent step is markedly improved.

The ozone-containing gas which can be used in step (1) is obtained by supplying air, oxygen or oxygen-containing gas to an ozone generator. The ozone-containing gas may be used as diluted with nitrogen, carbonic acid gas, air, etc. The ozone concentration in the ozone-containing gas is generally from 0.01 to 5.0 vol %, and preferably from 0.1 to 2.0 vol %. If it is too low, the contact time or the size of the reactor must be increased, or loss of acetonitrile by entrainment with the exhaust gas is increased, only resulting in a reduction in efficiency. It is generally difficult to increase the ozone concentration over 5 vol % from the performance of the ozone generator.

The contact temperature is generally from −40° to 80° C., and preferably from 10° to 40° C. At lower temperatures, the reaction tends to be retarded, or trace components are precipitated. At too high temperatures, the reaction excessively proceeds only to reduce the acetonitrile yield.

The contact may be carried out under reduced pressure, atmospheric pressure or pressure and preferably under a pressure between atmospheric pressure and 10 atm.

The contact may be either in a batch system or a continuous system. Contact in a batch system can be effected by means of a single- or multi-stage contact tank or bubbling tower equipped with a stirrer. For ensuring efficient gas-liquid contact, a contact tank equipped with a stirrer is preferred. Further, for obtaining good gas-liquid contact, the ozone-containing gas is preferably fed from at least one nozzle into crude acetonitrile as small bubbles. The ozone-containing gas is preferably fed from the position below or beside a stirring wing. The optimum position and number of the nozzles are decided according to the structure of the tank and stirring wing and based on observation of the stirring state of acetonitrile.

A contact treatment in a batch system is suitably carried out by feeding an ozone-containing gas in an amount of from 1 to 10000, preferably from 10 to 1000, times the volume of crude acetonitrile for a period of from 1 to 300 minutes, preferably from 10 to 120 minutes, while varying depending on the amount of impurities in the crude acetonitrile. If the feeding time is too short, the reaction between ozone and the impurities is insufficient, and the loss of acetonitrile due to entrainment is increased with the increased flow rate of the gas. Too long a feeding time has no merit from the standpoint of productivity.

The feeding time of an ozone-containing gas may also be decided by analyzing the ozone concentration in the exhaust gas. In this case, the feed can be continued until the ozone concentration in the exhaust gas reaches at least 80%, preferably at least 90%, of that in the gas introduced. The ozone concentration may be analyzed by means of a continuous analyzer utilizing iodometric titration, ultraviolet photometric titration or chemiluminescence analysis.

The contact treatment in a continuous system may be carried out in a packed tower, a wetted-wall tower, a bubbling tower, etc. A packed tower is preferred. Suitable packing includes Rasching ring, Lessing ring, Berl saddle, interlock saddle, terralet packing, pole ring, MacMahon packing, Dixon ring, etc., which may be made of porcelain, metals, plastics, carbon, etc. The contact may be either in a counter-current system or a parallel-current system, and preferably in a counter-current system. In using a packed tower, a liquid redistribution plate may be provided at an appropriate height to improve the gas-liquid contact efficiency. A volume ratio of an ozone-containing gas to crude acetonitrile can be selected from 1 to 10000, and preferably from 10 to 1000, so as not to cause flooding.

Step (2) consists of contacting the acetonitrile from step (1) with a solid base.

The contact between the acetonitrile and a solid base is generally carried out at a temperature of from −40 to 80° C., preferably from 5 to 60° C., and more preferably from 10 to 40° C.

An anion exchange resins as the solid base include porous type or gel type strongly basic or weakly basic anion exchange resins. Both of ion exchange resins for aqueous solutions and those for non-aqueous solutions can be used. Strongly basic anion exchange resins are preferably used with the exchange group thereof, e.g., a trimethylammonium group or a dimethylethanol group, converted into an OH type or a $CO_3$ type by a regeneration treatment. Weakly basic anion exchange resins are preferably used with the exchange group thereof, e.g., a primary, secondary or tertiary amino group, regenerated with NaOH, NH$_4$OH, etc. It is recommended that these anion exchange resins, after being treated with a regenerant, are previously washed with an ample amount of acetonitrile to remove water or impurities present therein.

The contact between the solid base and acetonitrile may be effected either in a continuous system or in a batch system. A continuous system is recommended for the treatment on an industrial scale.

A contact treatment in a continuous system can be carried out by passing acetonitrile through a tower or pipe packed with a solid base at a space velocity of from 0.001 to 1000 (l/min), and preferably from 0.01 to 100 (l/min).

A contact treatment in a batch system can be carried out in a contact tank, etc. equipped with a stirrer or a shaker. A contact time is from 0.1 to 1000 minutes, and preferably from 1 to 120 minutes.

Step (3) of the present invention is a step in which low-boiling compounds and high-boiling compounds present in the acetonitrile from step (1) or (2) are separated and removed. The object of step (3) is to remove impurities inclusive of compounds causing UV absorption to afford highly purified acetonitrile having an absorbance of not more than 0.05 at 200 to 400 nm.

Separation of these impurities can be effected by distillation or membrane separation. For industrial separation, distillation is preferred.

A distillation tower which can be used in step (3) includes plate towers and packed towers. Examples of suitable plate towers include cross-current contact type plate towers with downcomers and counter-current contact type plate towers with no downcomer. The trays of the plate towers include a bubble cap tray, a perforated tray, and a valve tray. The number of plates is usually at least 10, and preferably from 30 to 80.

Examples of suitable packing for packed towers are Rasching ring, Lessing ring, pole ring, Berl saddle, interlock saddle, terralet packing, MacMahon packing, and Dixon ring, which may be made of porcelain, metals, plastics, carbon, etc. The gas-liquid contact efficiency may be improved by providing a liquid redistribution plate at an appropriate height.

Step (3), in which low-boiling compounds and high-boiling compounds are separated from acetonitrile, can be performed by means of two distillation towers connected in series. Specifically, low-boiling compounds are removed from the top of a first tower, and high-boiling compounds are withdrawn from the bottom of a second tower while recovering purified acetonitrile from the top of the second tower; or high-boiling compounds are separated from the bottom of a first tower, and low-boiling compounds are separated from the top of a second tower while recovering purified acetonitrile from the bottom of the second tower or an upper part thereof. For improving the quality of acetonitrile, it is preferable to first separate a water content as an azeotrope with acetonitrile and then acetonitrile is recovered from the top of a second tower. That is, low- boiling compounds are separated from the top of a first tower, and high-boiling compounds are separated from the bottom of a second tower while recovering purified acetonitrile from the top of the second tower. The water content as above referred to includes water originated in the crude acetonitrile and water by-produced by the ozone oxidation.

The removal of the low-boiling compounds and high-boiling compounds can be carried out by using a single distillation tower. Specifically, acetonitrile is introduced into the middle part of a distillation tower, and low-boiling compounds and high boiling compounds are separated from the top and the bottom, respectively, while recovering purified acetonitrile from the position higher or lower, preferably higher, than the position where acetonitrile is introduced.

In carrying out the distillation, a reflux ratio and rates of withdrawal of low-boiling compounds and high-boiling compounds are selected according to the desired degree of purification. The rates of withdrawal of the low-boiling compound-containing distillate and the high-boiling compound-containing bottom are at least 1%, and preferably at east 5%, based on the introduced acetonitrile. When the rate of withdrawal from the top or bottom is lower than 1%, the recovered acetonitrile sometimes has a UV absorbance of more than 0.05 at 200 to 400 nm due to trace amounts of residual impurities.

Removal of low-boiling compounds and high-boiling compounds may be effected using three or more distillation towers, but such brings no economical merit.

The above-mentioned distillation may be conducted under a pressure of from 0.5 to 10 atm, and is preferably carried out under a pressure of from ordinary pressure to 10 atm.

The above-mentioned three steps should be kept under precise and highly technical control particularly for obtaining acetonitrile suitable as a mobile phase solvent for HPLC. Such operative control can effectively be maintained by, for example, monitoring physical properties of crude acetonitrile as a starting material as well as the product of each step by near infrared spectrophotometry.

The objects of the present invention can be achieved if the order of step (2) and step (3) is replaced with each other.

The present invention will now be illustrated in greater detail by way of Examples, but it should be understood that the present invention is not construed as being limited thereto.

EXAMPLE 1

Crude acetonitrile having a UV absorbance of 1.703 at 200 nm and containing 3.5 ppm of acrylonitrile, 8 ppm of methacrylonitrile, 8 ppm of allyl alcohol, and 2 ppm of oxazole as impurities was used as a starting material.

As step (1), from the top of an ozone contact tower having a diameter of 30 mm packed with porcelain Rasching rings (outer diameter: 5 mm; inner diameter: 2 mm; height: 5 mm) to a height of 410 mm was fed the crude acetonitrile under atmospheric pressure at 20° C. at a rate of 300 ml/hr, and from the bottom was fed an ozone-containing gas having an ozone concentration of 0.24 vol % (5.1 g/Nm$^3$; "Nm$^3$" means "m$^3$" at 0° C. and 1 atm) at a rate of 180 Nl/hr ("Nl" means liter at 0° C. and 1 atm) (gas/liquid ratio: 600). From the bottom of the tower was withdrawn acetonitrile having contacted with ozone.

As step (2), the acetonitrile from step (1) was subsequently fed to a column having a diameter of 20 mm packed with 50 ml of a non-aqueous porous type weakly basic anion exchange resin "Amberlist A21" at 20° C.

As step (3), the acetonitrile from step (2) was subsequently fed to the 10th plate of a distillation tower (diameter: 40 mm) having 65 perforated plates in total while maintaining the tower top pressure at atmospheric pressure and the reflux ratio at 16. Acetonitrile containing low-boiling compounds was distilled off from the top at a rate of 20% based on the supplied acetonitrile, and acetonitrile containing high-boiling compounds was withdrawn from the bottom at a rate of 10% based on the supplied acetonitrile while recovering purified acetonitrile from the 40th plate at a rate of 70% based on the supplied acetonitrile.

The resulting purified acetonitrile had a UV absorbance of 0.021 at 200 nm and not more than 0.013 at 210 to 400 nm. As a result of gas chromatography, acrylonitrile, methacrylonitrile, allyl alcohol, and oxazole were below the respective detection limit.

The above-described operation could be continued over 200 hours in a stable manner without any trouble to yield purified acetonitrile with stable physical properties underline system control on all steps with a near infrared spectrometer "Model 6500" manufactured by NIR Systems Co.

BRIEF DESCRIPTION OF THE DRAWINGS

The ultraviolet absorption spectrum each of the purified acetonitrile and the crude acetonitrile is shown in FIGS. 1 and 2, respectively.

EXAMPLE 2

Figure 1:
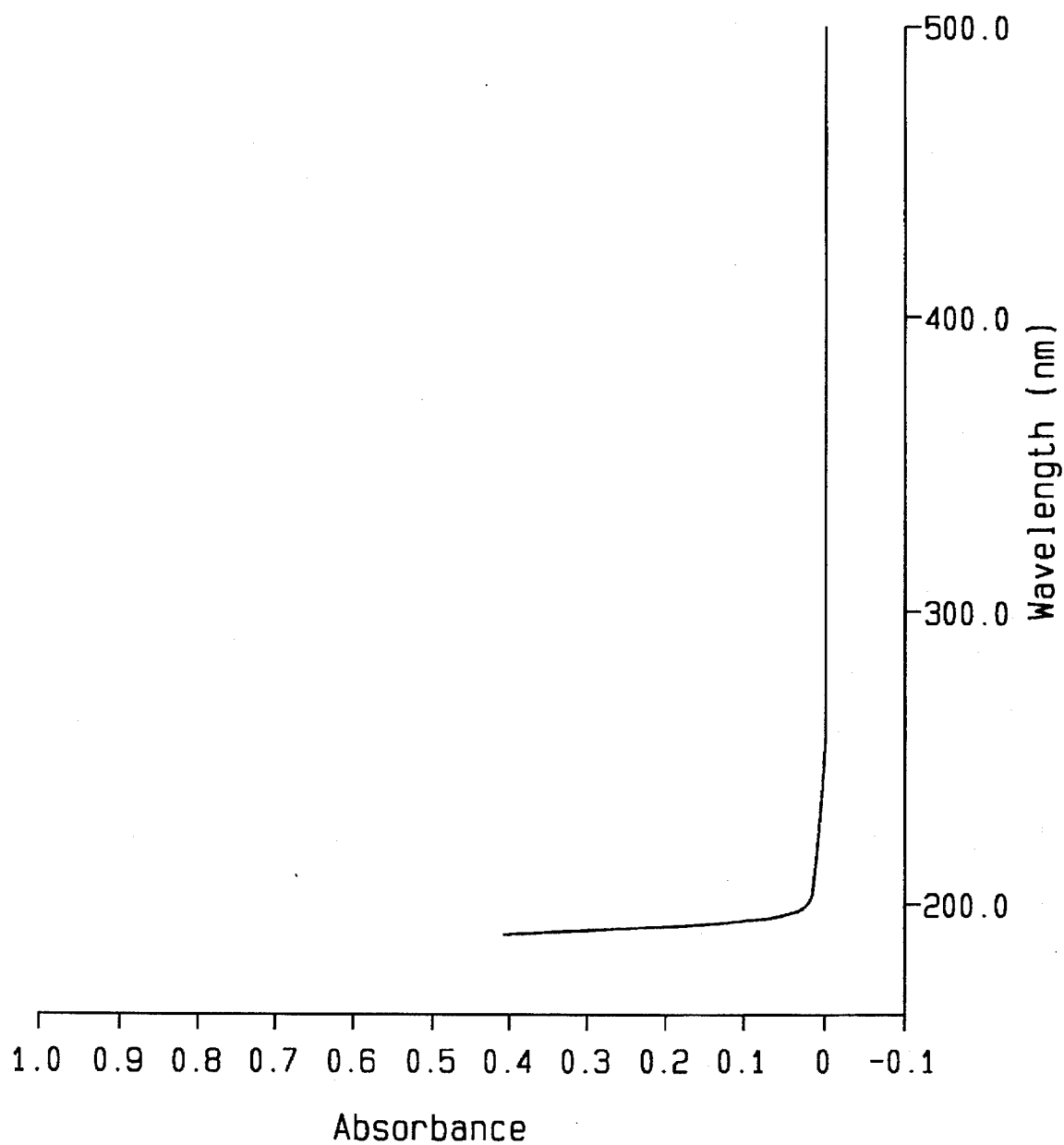
Figure 2:
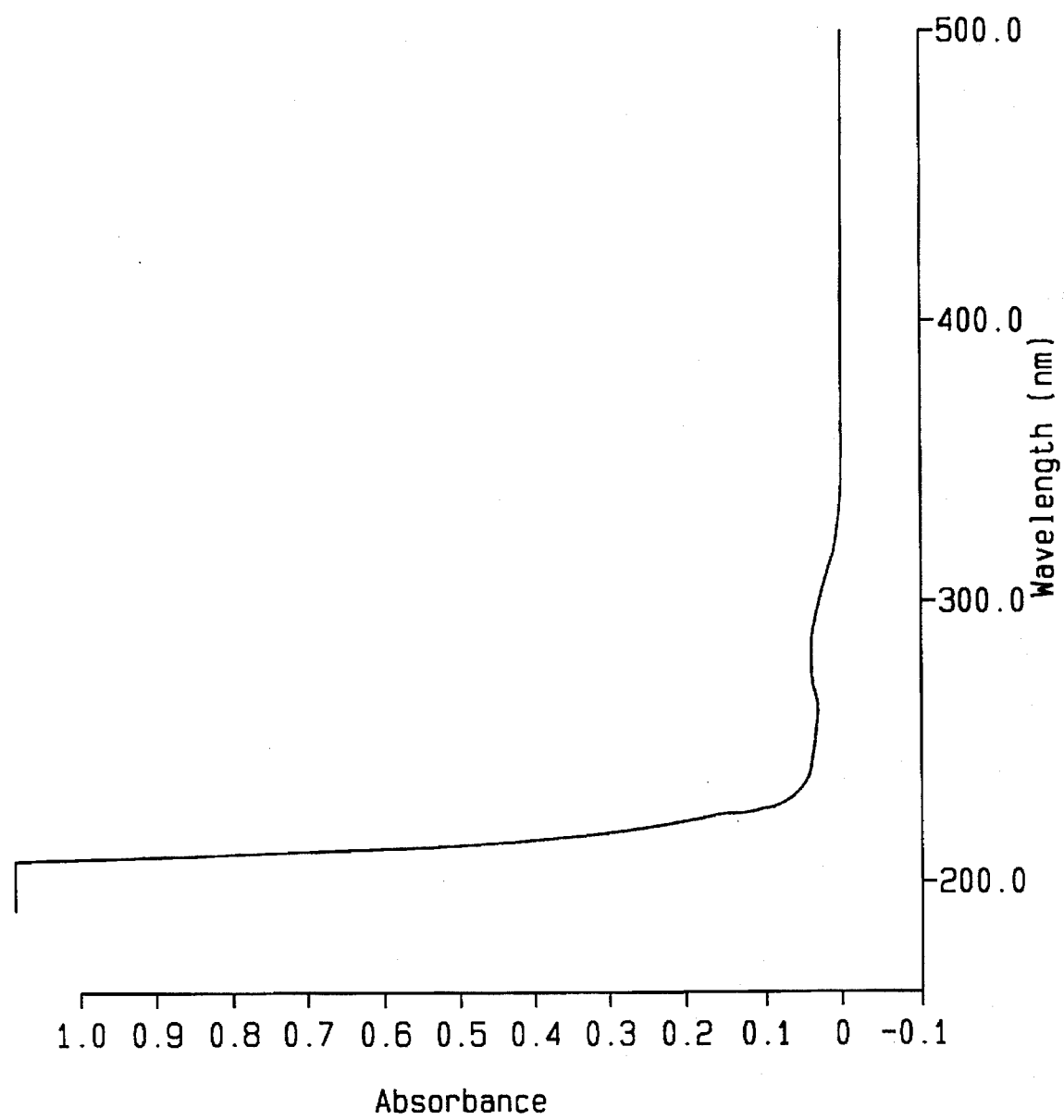

Purified acetonitrile was obtained in the same manner as in Example 1, except for using, as a solid base in step (2), 50 ml of a gel type strongly basic anion exchange resin "IRA-400" having its exchange group converted to an OH type. The UV absorbance of the resulting purified acetonitrile was 0.040 at 200 nm and not more than 0.025 at 210 to 400 nm.

COMPARATIVE EXAMPLE 1

Crude acetonitrile was purified in the same manner as in Example 1, except that step (1), i.e., contact with ozone, was not conducted. The resulting acetonitrile had a UV absorbance of 1.601 at 200 nm.

COMPARATIVE EXAMPLE 2

Crude acetonitrile was purified in the same manner as in Example 1, except that step (2), i.e., contact with a solid base, was not conducted. The resulting acetonitrile had a UV absorbance of 0.157 at 200 nm.

COMPARATIVE EXAMPLE 3

Crude acetonitrile was purified in the same manner as in Example 1, except that step (3), i.e., distillation, was not conducted. The resulting acetonitrile had a UV absorbance of 1.451 at 200 nm.

The results of the above three Comparative Examples reveal that omission of any one of steps (1) to (3) of the present invention results in a failure of obtaining acetonitrile having an absorbance of not more than 0.05 at 200 nm.

COMPARATIVE EXAMPLE 4

Acetonitrile was purified in the same manner as in Example 1, except that the operation was conducted in the order of step (2), step (3) and step (1). The resulting acetonitrile had a UV absorbance of 1.655 at 200 nm.

COMPARATIVE EXAMPLE 5

Acetonitrile was purified in the same manner as in Example 1, except that the operation was conducted in the order of step (2), step (1) and step (3). The resulting acetonitrile had a UV absorbance of 0.219 at 200 nm.

COMPARATIVE EXAMPLE 6

Acetonitrile was purified in the same manner as in Example 1, except that the operation was conducted in the order of step (3), step (1) and step (2) The resulting acetonitrile had a UV absorbance of 1.552 at 200 nm.

COMPARATIVE EXAMPLE 7

Acetonitrile was purified in the same manner as in Example 1, except that the operation was conducted in the order of step (3), step (2) and step (1) The resulting acetonitrile had a UV absorbance of 1.550 at 200 nm.

EXAMPLE 3

Acetonitrile by-produced in the production of acrylonitrile by ammoxydation of propylene was recovered and purified to have a UV absorbance of 0.360 at 200 nm was used as crude acetonitrile. In a 3 l round flask equipped with a stirrer was put 2000 ml of the crude acetonitrile, and gas containing 0.24 vol % of ozone was fed thereto at a rate of 3 Nl/min at 20° C. The feed of the ozone-containing gas was ceased when the ozone concentration in the exhaust gas reached 0.20 vol % which corresponded to 83% of that of the gas fed. The resulting acetonitrile was treated in the same manner as in steps (2) and (3) of Example 1 to furnish purified acetonitrile having a UV absorbance of 0.040 at 200 nm and not more than 0.026 at 210 to 400 nm.

EXAMPLE 4

Purified acetonitrile was obtained in the same manner as in Example 1, except that in step (1) 1 l of the acetonitrile was added to a 2 l round bottom flask equipped with a stirrer, and 1.09 g of potassium permanganate (produced by Wako Pure Chemicals Co., Ltd.) as a compound generating nascent oxygen, followed by stirred for 2 hours at 60° C., to obtain acetonitrile containing no potassium permanganate; and then the same operation as in step (2) and step (3) was carried out. The resulting purified acetonitrile had a UV absorbance of 0.045 at 200 nm, and not more than 0.027 at 210 to 400 nm.

EXAMPLE 5

Purified acetonitrile was obtained in the same manner as in Example 1, except that the operation was conducted in the order of step (1), step (3) and step (2) The resulting purified acetonitrile had a UV absorbance of 0.048 at 200 nm and not more than 0.028 at 210 to 400 nm.

As described in Examples 1 to 5, highly purified acetonitrile having a UV absorbance of not more than 0.05 at 200 nm were obtained through simple operation.

According to the present invention, highly purified acetonitrile having an absorbance of not more than 0.05 at an ultraviolet wavelength of from 200 to 400 nm, which can be used as a mobile phase solvent of HPLC, can be obtained by a process comprising step (1) in which crude acetonitrile is brought into contact with nascent oxygen, step (2) in which the acetonitrile is brought into contact with at least one substance selected from a solid base and an adsorbent, and step (3) in which low-boiling compounds and high-boiling compounds are separated and removed; or a process comprising step (1), step (3) and step (2) in this order.

While the invention has been described in detail and with reference to specific examples thereof, it will be apparent to one skilled in the art that various changes and modifications can be made therein without departing from the spirit and scope thereof.

What is claimed is:

1. A process for purifying crude acetonitrile having a UV absorbance at 200 nm of from 0.1 to 5 comprising:
   (1) a step of contacting crude acetonitrile with an ozone-containing gas in an amount from 1 to 10,000 times the volume of the crude acetonitrile,
   (2) a step of contacting the acetonitrile from step (1) with an anion exchange resin, wherein the contact temperature of the acetonitrile and the anion exchange resin is from −40° to 80° C.,
   (3) a step of removing low-boiling compounds and high-boiling compounds from the acetonitrile.

2. A process as claimed in claim 1, wherein said crude acetonitrile has an absorbance of not less than 0.1 at a wavelength of 200 nm and the purified acetonitrile has an absorbance of not more than 0.05 at a wavelength of from 200 to 400 nm.

3. A process as claimed in claim 1, wherein said crude acetonitrile is acetonitrile recovered as a by-product in the production of acrylonitrile or methacrylonitrile by catalytic ammoxydation of propylene, isobutene or t-butyl alcohol with ammonia and molecular oxygen.

4. A process as claimed in claim 2, wherein the nascent oxygen is nascent oxygen generated from at least one compound selected from a permanganic acid or a salt thereof, an oxyacid or a salt thereof, a peroxide, and an ozone-containing gas.

5. A process as claimed in claim 4, wherein said peroxide is selected from hydrogen peroxide, sodium peroxide, and barium peroxide.

6. A process as claimed in claim 4, wherein said oxyacid or a salt thereof is at least one selected from sodium hypochlorite, potassium hypochlorite, sodium hypoiodite, potassium hypoiodite, sodium hypobromite, potassium hypobromite, sodium chlorate, potassium chlorate, sodium iodate, potassium iodate, sodium bromate, potassium bromate, sodium perchlorate, potassium perchlorate, perchloric acid, periodic acid, sodium periodate, and potassium periodate.

7. A process as claimed in claim 2, wherein the contact with nascent oxygen is carried out at a temperature of from −40° to 80° C. in a batch system or a continuous system.

8. A process as claimed in claim 3, wherein the contact with nascent oxygen is carried out at a temperature of from −40° to 80° C. in a batch system or a continuous system.

9. A process as claimed in claim 7, wherein said nascent oxygen is an ozone-containing gas having an ozone concentration of from 0.01 to 5.0% by volume.

10. A process as claimed in claim 8, wherein said nascent oxygen is an ozone-containing gas having an ozone concentration of from 0.01 to 5.0% by volume.

11. A process as claimed in claim 9, wherein the contact with said ozone-containing gas is carried out in a batch system by feeding the ozone-containing gas in an amount from 1 to 10000 times as much as the volume of the crude acetonitrile from at least one nozzle into the liquid crude acetonitrile for a period of from 1 to 300 minutes.

12. A process as claimed in claim 10, wherein the contact with said ozone-containing gas is carried out in a batch system by feeding the ozone-containing gas in an amount from 1 to 10000 times as much as the volume of the crude acetonitrile from at least one nozzle into the liquid crude acetonitrile for a period of from 1 to 300 minutes.

13. A process as claimed in claim 9, wherein the contact with said ozone-containing gas is carried out in a batch system by feeding the ozone-containing gas until the ozone concentration in the exhaust gas reaches at least 80% of that of the gas fed.

14. A process as claimed in claim 10, wherein the contact with said ozone-containing gas is carried out in a batch system by feeding the ozone-containing gas until the ozone concentration in the exhaust gas reaches at least 80% of that of the gas fed.

15. A process as claimed in claim 9, wherein the contact with said ozone-containing gas is carried out in a continuous system in a packed tower or a plate tower by feeding the crude acetonitrile and the ozone-containing gas from the top and the bottom of the tower, respectively, at a gas to liquid volume ratio of from 1 to 10000.

16. A process as claimed in claim 10, wherein the contact with said ozone-containing gas is carried out in a continuous system in a packed tower or a plate tower by feeding the crude acetonitrile and the ozone-containing gas from the top and the bottom of the tower, respectively, at a gas to liquid volume ratio of from 1 to 10000.

17. A process as claimed in claim 2, wherein the contact with the solid base is carried out at a temperature of from −40° to 80° C.

18. A process as claimed in claim 3, wherein the contact with the solid base is carried out at a temperature of from −40° to 80° C.

19. A process as claimed in claim 17, wherein said anion exchange resin is a porous or gel type strongly basic anion exchange resin having an OH type or $CO_3$ type exchange group or a porous or gel type weakly basic anion exchange resin having a primary, secondary or tertiary amino group as an exchange group.

20. A process as claimed in claim 18, wherein said anion exchange resin is a porous or gel type strongly basic anion exchange resin having an OH type or $CO_3$ type exchange group or a porous or gel type weakly basic anion exchange resin having a primary, secondary or tertiary amino group as an exchange group.

21. A process as claimed in claim 2, wherein said step of removing low-boiling compounds and high-boiling compounds is carried out by at least one of distillation and membrane separation.

22. A process as claimed in claim 3, wherein said step of removing low-boiling compounds and high-boiling compounds is carried out by at least one of distillation and membrane separation.

23. A process as claimed in claim 21, wherein said step of removing low-boiling compounds and high-boiling compounds is carried out in a plate tower or a packed tower under a pressure of from 0.5 to 10 atm.

24. A process as claimed in claim 22, wherein said step of removing low-boiling compounds and high-boiling compounds is carried out in a plate tower or a packed tower under a pressure of from 0.5 to 10 atm.

25. A process as claimed in claim 21, wherein said step of removing low-boiling compounds and high-boiling compounds is carried out in two distillation towers, in which low-boiling compounds are separated by a first tower, and high-boiling compounds are separated by a second tower.

26. A process as claimed in claim 22, wherein said step of removing low-boiling compounds and high-boiling compounds is carried out in two distillation towers, in which low-boiling compounds are separated by a first tower, and high-boiling compounds are separated by a second tower.

27. A process as claimed in claim 21, wherein said step of removing low-boiling compounds and high-boiling compounds is carried out in a single distillation tower, in which acetonitrile is introduced into the middle part of the tower, and low-boiling compounds and high-boiling compounds are separated from the top and the bottom of the tower, respectively, while recovering purified acetonitrile from the position higher than the position where acetonitrile is introduced.

28. A process as claimed in claim 22, wherein said step of removing low-boiling compounds and high-boiling compounds is carried out in a single distillation tower, in which acetonitrile is introduced into the middle part of the tower, and low-boiling compounds and high-boiling compounds are separated from the top and the bottom of the tower, respectively, while recovering purified acetonitrile from the position higher than the position where acetonitrile is introduced.

29. A process as claimed in claim 1, wherein each step is controlled by near infrared spectrophotometry.

* * * * *